Dec. 20, 1949. H. C. SWIM Plant Pat. 908
RASPBERRY PLANT
Filed Nov 29, 1948
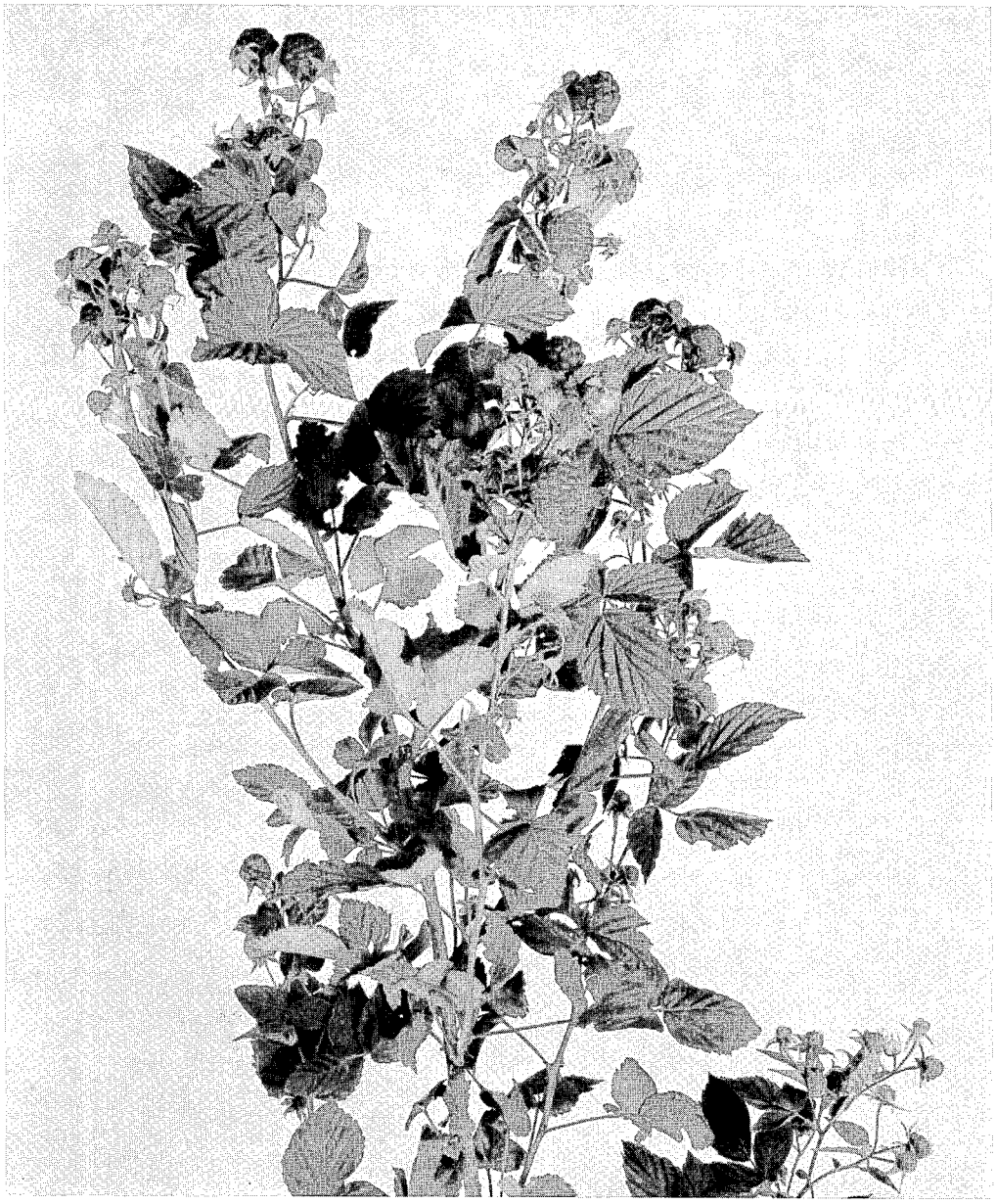
Inventor
H. C. Swim
By Robb & Robb,
Attorneys Patented Dec. 20, 1949 Plant Pat. 908

UNITED STATES PATENT OFFICE

908

RASPBERRY PLANT

Herbert C. Swim, Ontario, Calif., assignor to Armstrong Nurseries, Inc., Ontario, Calif., a corporation of California Application November 29, 1948, Serial No. 62,457

1 Claim. (Cl. 47—62)

The present invention relates to a new and distinct variety of raspberry plant resulting from crossing the known varieties "Sunrise" × "Washington."

This new variety is the result of definite breeding efforts to improve certain important characteristics of its parents and to combine in the hybrid as many of their commercially desirable habits of growth, productivity, attractive appearance, quality of taste, etc., as possible, whereby this red raspberry will be particularly suited for the climate of Southern California.

My objectives have been fully achieved so that I am able to define more specifically the following combination of distinctive characteristics as especially applicable to this red variety:

(1) A plant with vigorous growth habit and with a winter chilling requirement of the lateral buds of the canes sufficiently low to make the variety ideally suited to such climatic areas as Southern California from the standpoint of both vegetative growth and fruit production. The leaf buds of most varieties of red raspberries now known to commerce require a longer chilling requirement than they receive in Southern California and similar climatic zones. As a consequence the lateral buds remain dormant throughout the growing season; this new variety produces lateral fruit clusters from almost every lateral bud on the cane with a resulting additional fruit production comparable to the additional number of lateral growths. This characteristic results in fruit production substantially greater than the best varieties now available for planting in Southern California.

(2) A very early ripening season approximately two to three weeks earlier than "Sunrise," now usually considered the earliest variety available, and with fruit somewhat larger than this parent variety.

(3) The long season of ripening for the principal crop in the spring and the tendency to continuity of fruit production throughout the remainder of the growing season. This is unlike any raspberry we now know in commerce.

This new variety of raspberry differs from its parents in the following characteristics:

(1) The variety "Sunrise" was introduced because of its earliness. This new variety begins to ripen its fruit from two to three weeks earlier than "Sunrise" in Southern California, and from four to five weeks ahead of the "Washington" variety.

(2) The plants are more vigorous in cane growth than either of the parents and produce a heavier crop than either parent.

(3) The winter chilling requirement of the lateral buds of this variety is substantially less than those of either of its parents causing it to leaf out and to begin to grow earlier in the spring in Southern California than either of its parent varieties. This low chilling requirement is also responsible for a greater number of lateral eyes growing and producing fruit, thereby causing a much heavier production in this new variety than in its parent varieties. Probably for the same reasons which result in greater thriftiness of vegetative growth, the fruit is larger than either of its parent varieties.

Asexual reproduction shows that these characteristics hold true through succeeding propagations.

The drawing illustrates a specimen of the new variety of red raspberry plant herein set forth, and shows particularly the erectness of growth habit and the habit of producing many clusters of berries as more specifically referred to hereinafter.

The following is a detailed description of the new variety, color terminology being in accordance with Ridgway's Color Standards and Nomenclature:

Breeding:

*Seedling.*—Cross of "Sunrise" × "Washington." The specimens described were grown at Ontario, California. Dates first and last picking—somewhat variable depending on the season, but usually first picking about May 25th to June 10th with first crop ending about August 1st. More or less continuous until November 15th, or until frost.

Plant: Large; vigorous; erect; dense; tall; very productive; regular bearer; deciduous.

Propagation: By suckers. Only method so far tried.

Environment: Sun; dry or moist climate; best in cool summer climate.

Canes: Slender; medium height; glabrous; hairy; prickly; pithy; stout.

*Color.*—Normal color—Kildare Green, Plate XXXI, on side exposed to sun, washed with Acajou Red, Plate XIII.

Thorns or prickles:

*Small prickles.*—Many; medium length; hooked downward slightly; with short, broad oval base. *Color*—Normal—Kildare Green, Plate XXXI, when exposed to sun, overlaid with Acajou Red, Plate XIII.

*Hairs.*—Many. *Color* — Whitish, nearly colorless.

New shoots:

*Color.*—Kildare Green, Plate XXXI; glossy.

*Small prickles.* — Many; short; hooked downward slightly; with short, broad oval base. *Color*—Acajou Red, Plate XIII.

*Hairs.* — Many; microscopic. *Color*—white to colorless.

*Tomentum.*—None.

*Bloom.*—None.

Foliage:

*Leaves.*—Compounded of three to five leaflets.

*Leaflets.*—Abundant; medium size; moderately thin; leathery; rugose. *Shape*—ovate with apex acute; base round; margin doubly dentate near apex, simply dentate at base. *Color*—mature—upper surface: Forest Green, Plate XVII; under surface: Tea Green, Plate XLVII. *Terminal leaflet measurements*—5 to 10 cm. from base to apex; 2½ to 7 cm. in breadth. *Lateral leaflets*—3½ to 8 cm. in length; 1½ to 5 cm. in breadth. *Color*—young—upper surface: Forest Green, Plate XVII; very young leaves streaked near margins with Acajou Red, Plate XIII. Under surface: Tea Green, Plate XLVII. *Variations*—young leaves glossy, otherwise same as mature leaves except for reddish tinge.

Rachis: Medium heavy; upper side, grooved, prickly; underside, moderately prickly.

Stipules: Long; very narrow; with moderately long points; irregularly formed, nearly parallel to stem.

Flowers borne: Five to ten in irregular cymose cluster; on normal long cyme; pedicelled; perfect; complete.

*Quantity of bloom.*—Abundant.

*Continuity.*—One long season in spring; more or less with lighter crop during remainder of growing season.

Flower:

*Pedicel.*—Medium to long; medium caliper; stiff; numerous short prickles. *Color*—Kildare Green, Plate XXXI; when exposed to sun, green is overlaid with Acajou Red, Plate XIII.

*Before calyx breaks.*—*Size*—small to medium. *Form*—pointed; few hairs on the surface of the bud.

*Calyx.*—Inner surface: With fine tomentum; margins lined with hairs. Outer surface: with short hairs.

*Bloom.*—Size, when fully open—medium; 1 cm. to 1½ cm. Petalage—single (1 row of petals). Petals arranged regularly—5 petals. *Form*—cupped.

Petals: Thin; leathery.

*Color.*—Outside and inside surface white.

Reproductive organs:

*Stamens.*—Many.

*Filaments.*—Medium to long; most with anthers.

*Anthers.*—Medium size.

*Pollen.*—Moderate to abundant.

*Pistils.*—Many.

*Sepals.* — Persistent; moderately long; straight but recurved as fruit ripens; 5 in number.

Fruit:

*Maturity when described.*—July 1st.

*Size of berry.*—1.5–2.10 cm. in length; uniform; large; diameter, 2 cm.; many clusters; 5–10 or more (sometimes 35 to 40) berries to cluster.

*Form of druplets.*—Uniform; symmetrical; broadly ovoid, nearly round in appearance from outside; moderate size; compact; druplets free of torus. Sterility—all druplets mature. Skin—medium thickness; tough to medium tough. Tomentum—hairs—moderate; does not rub off easily; minute white fuzz, hardly noticeable without magnification.

*Color of ripe berry.*—Currant Red, Plate 821/3, page 167, Wilson's Horticultural Colour Chart II.

*Ripening.*—Began May 21st; ripening peak June 20th. Ripening end—end of first crop August 1st with second crop from October 1st to November 15th.

*Ripens.*—Even.

*Texture.*—Firm; meaty.

*Flavor.*—Subacid.

*Aroma.*—Distinct.

*Eating quality.*—Excellent.

*Cooking quality.*—Good.

Seeds:

*Size.* — Medium. Length — 2½ cm. Breadth—1–1½ cm.

*Form.*—Oval in lateral cross section; somewhat reniform in longitudinal cross section.

Use: Market; local; dessert; culinary.

Keeping quality: Good.

Shipping quality: Good. Berry holds shape on picking; holds together after picking.

Disease: Resistant to mildew and rust.

I claim:

A new and distinct variety of raspberry plant characterized as to novelty by its vigorous habit of growth, low winter chilling requirement of the lateral buds of the canes, production of lateral fruit clusters from practically all lateral buds on the canes resulting in high production of fruit, and early and long ripening season with a tendency to continuity of fruit production throughout the remainder of the growing season, substantially as shown and described.

HERBERT C. SWIM.

No references cited.